(12) United States Patent
Liu et al.

(10) Patent No.: US 8,358,880 B2
(45) Date of Patent: Jan. 22, 2013

(54) HYBRID COUPLING STRUCTURE OF THE SHORT RANGE PLASMON POLARITON AND CONVENTIONAL DIELECTRIC WAVEGUIDE, A COUPLING STRUCTURE OF THE LONG RANGE PLASMON POLARITON AND CONVENTIONAL DIELECTRIC WAVEGUIDE, AND APPLICATIONS THEREOF

(75) Inventors: Fang Liu, Beijing (CN); Rui-Yuan Wan, Beijing (CN); Yi-Dong Huang, Beijing (CN); Xue Feng, Beijing (CN); Wei Zhang, Beijing (CN); Jiang De Peng, Beijing (CN); Yoshikatsu Miura, Kyoto (JP); Daisuke Niwa, Kyoto (JP); Dai Ohnishi, Kyoto (JP)

(73) Assignees: Rohm Co., Ltd., Kyoto (JP); Tsinghua University, Beijing (CN)

(*) Notice: Subject to any disclaimer, the term of this patent is extended or adjusted under 35 U.S.C. 154(b) by 375 days.

(21) Appl. No.: 12/639,549

(22) Filed: Dec. 16, 2009

(65) Prior Publication Data
US 2010/0310205 A1  Dec. 9, 2010

(30) Foreign Application Priority Data

Dec. 16, 2008 (CN) .......................... 2008 1 0186418
Apr. 7, 2009 (CN) .......................... 2009 1 0132692

(51) Int. Cl.
*G02F 1/035* (2006.01)
(52) U.S. Cl. ......................................................... 385/2
(58) Field of Classification Search ....................... 385/2
See application file for complete search history.

(56) References Cited

U.S. PATENT DOCUMENTS

| | | | |
|---|---|---|---|
| 5,729,641 A * | 3/1998 | Chandonnet et al. | 385/2 |
| 6,741,782 B2 * | 5/2004 | Berini | 385/130 |
| 6,782,179 B2 * | 8/2004 | Bozhevolnyi et al. | 385/131 |
| 7,864,313 B2 * | 1/2011 | Baumberg et al. | 356/301 |
| 7,949,210 B2 * | 5/2011 | Durfee et al. | 385/1 |
| 2007/0146866 A1 * | 6/2007 | Wright | 359/332 |
| 2007/0196067 A1 * | 8/2007 | Lee et al. | 385/131 |
| 2008/0008418 A1 * | 1/2008 | Smith et al. | 385/32 |
| 2010/0014808 A1 * | 1/2010 | Flammer | 385/37 |

OTHER PUBLICATIONS

Wan, R., et al., "Ultrathin layer sensing based on hybrid coupler with short-range surface plasmon polariton and dielectric waveguide", Optics Letter, vol. 35, No. 2, 2010.*
Liu, F., et al., "Hybrid coupling between long-range surface plasmon polariton mode and dielectric waveguide mode", J. of Ligthwave Tech., vol. 29, No. 9, 2011.*
Wan, R., et al., "Vertical coupling between short range plasmon polariton mode and dielectric waveguide mode", Applied Physics Letter 94, 141104 (2009).*

* cited by examiner

*Primary Examiner* — Charlie Peng
(74) *Attorney, Agent, or Firm* — Fish & Richardson P.C.

(57) ABSTRACT

The present invention provides a hybrid coupling structure of a short range surface plasmon polariton and a conventional dielectric waveguide, including a dielectric substrate layer, a dielectric waveguide layer positioned on the said dielectric substrate layer, a coupling matching layer positioned on the said dielectric waveguide layer and a short range surface plasmon waveguide portion, formed on the said coupling matching layer, for conducting the short range surface plasmon polariton. The present invention also provides a coupling structure of a long range surface plasmon polariton and a dielectric waveguide, including a dielectric substrate layer, a dielectric waveguide layer, a coupling matching layer and a long range surface plasmon waveguide portion upward from below respectively.

2 Claims, 12 Drawing Sheets

HYBRID COUPLING STRUCTURE OF THE SHORT RANGE PLASMON POLARITON AND CONVENTIONAL DIELECTRIC WAVEGUIDE, A COUPLING STRUCTURE OF THE LONG RANGE PLASMON POLARITON AND CONVENTIONAL DIELECTRIC WAVEGUIDE, AND APPLICATIONS THEREOF

BACKGROUND OF THE INVENTION

1. Field of the Invention

The present invention relates to the field of the photoelectron technique, and more specifically, it relates to a hybrid coupling structure of a short range surface plasmon polariton and a conventional dielectric waveguide and a coupling structure of a long range surface plasmon polariton and a dielectric waveguide, as well as a refractive index sensor, a TM polarization modulator etc. based on the structures.

2. Description of the Background Art

A surface plasmon polariton (SPP) is an electromagnetic field propagating along the interface between a metal and a dielectric. As shown in FIG. 1, 1 denotes a metal (or a mixture of a metal and a dielectric), 2 denotes dielectrics around the metal and numeral 3 denotes surface plasmon polaritons on interfacial portions, and coupling develops in the SPPs on the upper and lower surfaces when the metal is sufficiently thin, to form a symmetric mode, i.e., a long range surface plasmon polariton 4, or an antisymmetric mode, i.e., a short range surface plasmon polariton 5.

An SPP is a surface wave, and the electromagnetic field energy thereof concentrates in the vicinity of the interface between a metal and a dielectric, while the amplitude of the electromagnetic field is exponentially attenuated following the distance separating from the interface in the dielectric. When a metal film is relatively thin, plasmon polaritons on the upper and lower surfaces develop coupling, and form two types of new surface plasmon polariton modes.

As shown in FIG. 2, one of the modes is the symmetric mode, whose mode field is mostly distributed in the dielectrics other than the metal, has relatively small propagation loss and is propagable over a relatively long distance along a metal film, and this type of mode is referred to as a long range surface plasmon polariton (LRSPP).

Another mode is the antisymmetric mode, which is more approximate to the metal, has relatively large propagation loss and is only propagable over an extremely short distance along the metal film, and hence the same is referred to as a short range surface plasmon polariton (SRSPP).

Thus, a thin metal or a metal strip becomes a surface plasmon waveguide (SPP waveguide). When propagating a long range or short range surface plasmon polariton, the same is referred to as a long range or short range surface plasmon waveguide.

When the distance between a metal waveguide and a dielectric waveguide is sufficiently small, a conventional dielectric waveguide mode develops coupling with an SPP mode under constant conditions. An SRSPP has a characteristic of approximating a metal at a higher degree as compared with SPP and LRSPP modes, and hence such a new coupling phenomenon that this type of SRSPP hybrid-couples with a dielectric waveguide renders the coupling length and the size of a device shorter and smaller respectively, and has wide-ranging applications in the field of a highly integrated photon device and optical communication.

Further, the electromagnetic field energy of the SPP concentrates in the vicinity of the interface between the metal and the dielectric, and hence the electromagnetic field on the metal surface is extremely strong and extremely sensitive to the form of the surface, particularly a change in the refractive index, and has wide-ranging applications in the biosensor field.

However, a wave field of a the short range SPP wave approximates a metal surface at a higher degree as compared with a conventional SPP wave and a mode characteristic thereof is extremely sensitive to a refractive index change in a dielectric in an ultrathin range around a metal film, and hence an obvious change is caused in the coupling of a short range surface plasmon polariton mode and a conventional dielectric waveguide mode and a drastic change in output power of the dielectric waveguide is caused if the refractive index of an ultrathin layer material above the metal film changes (the most biological reactions belong to this type of ultrathin layer reaction). This provides a new way for high precision detection of the refractive index of the ultrathin layer material.

A conventional biosensor of a surface plasmon polariton requires separate components such as a prism and a rotation table, and hence the same has a large volume, is not only hard to control but also has low detection sensitivity with respect to an ultrathin layer material, is inferior in stability and requires a high cost, whereby spreading/application thereof is strictly limited.

SUMMARY OF THE INVENTION

<Hybrid Coupling Structure of Short Range Surface Plasmon Polariton and Conventional Dielectric Waveguide>

An object of the present invention is to provide a hybrid coupling structure of a short range surface plasmon polariton and a conventional dielectric waveguide, for achieving advanced hybrid integration of a surface plasmon polariton-based device and a dielectric-based device and achieving various types of controllable photoelectric integrated devices.

Another object of the present invention is to provide a highly integrated short range surface plasmon polariton hybrid coupler, for rendering mutual conversion of two types of waves implementable through high efficiency coupling of a short range surface plasmon polariton and a TM wave of a conventional dielectric waveguide.

Still another object of the present invention is to provide a highly integrated short range surface plasmon polariton hybrid polarizer, for attaining an object of outputting a TE polarized wave by eliminating a TM wave in an extremely short propagation distance on the basis of high loss of a short range surface plasmon polariton and an ultrashort hybrid coupling length.

A further object of the present invention is to provide a highly integrated short range surface plasmon polariton hybrid coupling sensor, for achieving high sensitivity real-time detection of an ultrathin dielectric refractive index and solving such problems in a conventional surface plasmon polariton refractive index detecting method that a volume is large, the number of required component devices is large, control is difficult, stability is inferior and detection sensitivity for an ultrathin layer material is low.

<Coupling Structure of Long Range Surface Plasmon Polariton and Dielectric Waveguide>

An object of the present invention is to provide a coupling structure of a long range surface plasmon polariton and a dielectric waveguide, for achieving high integration of a long range surface plasmon polariton-based device and a dielectric-based device and achieving a refractive index-detectable and controllable photoelectric integrated device.

Another object of the present invention is to provide a refractive index sensor for achieving high sensitivity real-time detection of a refractive index and solving such problems in a conventional method of detecting the refractive index of a surface plasmon polariton that a volume is large, the number of required component devices is large, control is difficult and stability is inferior.

Still another object of the present invention is to provide a photoelectric intensity modulator of low power consumption and high performance.

<Hybrid Coupling Structure of Short Range Surface Plasmon Polariton and Conventional Dielectric Waveguide>

In order to attain the aforementioned objects, a hybrid coupling structure of a short range surface plasmon polariton and a conventional dielectric waveguide is provided according to the present invention, and in the aforementioned coupling structure, a dielectric substrate layer, a dielectric waveguide layer positioned on the aforementioned dielectric substrate layer, a coupling matching layer positioned on the aforementioned dielectric waveguide layer and a short range surface plasmon waveguide portion, formed on the aforementioned coupling matching layer, for conducting the short range surface plasmon polariton are included.

Preferably, the refractive index of the aforementioned dielectric waveguide layer is larger than the refractive index of the aforementioned dielectric substrate layer, and the refractive index of the aforementioned coupling matching layer is smaller than the refractive index of the aforementioned dielectric waveguide layer.

Preferably, selection of the refractive index of the aforementioned dielectric waveguide layer equalizes the equivalent refractive index of a base mode of a TM polarized state of the aforementioned dielectric waveguide layer with the equivalent refractive index of the aforementioned short range surface plasmon polariton.

Preferably, the refractive index of the aforementioned dielectric waveguide layer is 1.2 to 3.8, and the thickness of the aforementioned dielectric waveguide layer is 10 nm to 5000 nm.

Preferably, the thickness of the aforementioned coupling matching layer is 0.01 μm to 10 μm, and the refractive index of the aforementioned coupling matching layer is 1.2 to 3.8.

Preferably, the aforementioned short range surface plasmon waveguide portion further includes a dielectric buffer layer, a metal layer and a dielectric cover layer successively formed from below.

Preferably, the aforementioned metal layer is an alloy consisting of one type or a plurality of types among gold, silver, aluminum, copper, iron, chromium, nickel and titanium.

Preferably, the thickness of the aforementioned metal layer is 10 nm to 100 nm, and the thickness of the aforementioned dielectric buffer layer is 10 nm to 5000 nm.

Preferably, the refractive index of the aforementioned dielectric cover layer is 1.0 to 3.8, and the refractive index of the aforementioned dielectric buffer layer is 1.0 to 3.8.

Preferably, the total thickness of the aforementioned coupling matching layer and the aforementioned dielectric buffer layer is larger than a critical thickness stopping coupling development of the dielectric waveguide and the short range surface plasmon polariton.

According to the present invention, a hybrid coupler to which the aforementioned hybrid coupling structure is applied is further provided, a TM polarized state mode of the aforementioned dielectric waveguide develops coupling with the short range surface plasmon polariton, and the length of the aforementioned coupling is 10 μm to 2000 μm.

According to the present invention, a hybrid polarizer to which the aforementioned hybrid coupling structure is applied is further provided, and a TM wave is attenuated by developing energy coupling with the short range surface plasmon polariton when a TM, TE polarized state hybrid input light is incident from an end face of the aforementioned dielectric waveguide layer, and an output wave is a TE polarized wave.

According to the present invention, a TM polarization modulator to which the aforementioned hybrid coupling structure is applied is further provided, the upper portion of the aforementioned dielectric cover layer is covered with an electrode consisting of gold and chromium, and modulation of TM polarization is implemented by applying a modulation voltage between the electrode and the metal layer in the short range surface plasmon polariton waveguide portion and further executing modulation on a power output of the dielectric waveguide.

Preferably, an electrooptic dielectric material is employed for the aforementioned dielectric cover layer.

According to the present invention, a sensor to which the aforementioned hybrid coupling structure is applied is further provided, alteration is caused in coupling efficiency for a TM mode of the dielectric waveguide and the short range surface plasmon polariton when a change is caused in the refractive index of the dielectric cover layer, and the change in the refractive index of the aforementioned dielectric cover layer is detected by measuring a change in output power of the dielectric waveguide.

Preferably, a small change in the refractive index caused by a biological reaction or a physical/chemical action is included in a small change in the refractive index of the aforementioned dielectric cover layer.

Preferably, a detectable refractive index range of the aforementioned dielectric cover layer is controlled by adjusting the refractive index and the thickness of the aforementioned dielectric buffer layer.

Preferably, the thickness of the dielectric cover layer detectable by the aforementioned sensor is ⅕ of a used wavelength to 500 μm.

<Coupling Structure of Long Range Surface Plasmon Polariton and Dielectric Waveguide>

In order to attain the aforementioned objects, the present invention employs the following technical ideas:

The present invention provides a coupling structure of a long range surface plasmon polariton and a dielectric waveguide, and the aforementioned structure includes a dielectric substrate layer, a dielectric waveguide layer, a coupling matching layer and a long range surface plasmon waveguide portion upward from below respectively.

Preferably, the refractive index of the aforementioned dielectric waveguide layer is larger than the refractive indices of the aforementioned dielectric substrate layer and the aforementioned coupling matching layer.

Preferably, the TM mode equivalent refractive index of a dielectric waveguide of the aforementioned dielectric waveguide layer is equal to the equivalent refractive index of the long range surface plasmon polariton.

Preferably, the refractive index of the aforementioned dielectric waveguide layer is 1.2 to 3.8, and the thickness of the aforementioned dielectric waveguide layer is 10 nm to 5000 nm.

Preferably, the refractive index of the coupling matching layer is 1.2 to 3.8, and the thickness of the coupling matching layer is 0.01 μm to 10 μm.

Preferably, the aforementioned long range surface plasmon waveguide portion further includes a dielectric buffer layer, a metal layer and a dielectric cover layer upward from below.

Preferably, the aforementioned metal layer is an alloy in which one type or a plurality of types among platinum, gold, silver, aluminum, copper, iron, chromium, nickel and titanium are combined, or an alloy of each of the aforementioned metals, or metal ceramic.

Preferably, the thickness of the aforementioned metal layer is 5 nm to 100 nm, and the thickness of the aforementioned dielectric buffer layer is 1 nm to 20 μm.

Preferably, the refractive index of the aforementioned dielectric buffer layer is 1.0 to 3.8, and the refractive index of the aforementioned dielectric cover layer is 1.0 to 3.8.

Preferably, the total thickness of the aforementioned coupling matching layer and the aforementioned dielectric buffer layer is larger than a critical thickness stopping coupling development of a dielectric waveguide TM mode and a long range surface plasmon polariton mode.

The present invention provides a refractive index sensor to which the coupling structure of the aforementioned long range surface plasmon polariton and the dielectric waveguide is applied, the aforementioned refractive index sensor is mainly constituted of the aforementioned coupling structure, and the aforementioned structure comprises a dielectric substrate layer, a dielectric waveguide layer, a coupling matching layer and a long range surface plasmon waveguide portion upward from below respectively.

Preferably, a detectable refractive index range of the aforementioned dielectric cover layer is controlled by adjusting the refractive index and the thickness of the aforementioned dielectric buffer layer.

The present invention provides a photoelectric intensity modulator to which the coupling structure of the aforementioned long range surface plasmon polariton and the dielectric waveguide is applied, the aforementioned photoelectric intensity modulator is mainly constituted of the aforementioned coupling structure, and the upper portion of the dielectric cover layer of the aforementioned coupling structure is covered with a metal electrode.

Preferably, a modulation voltage is applied between the aforementioned metal electrode and the metal layer in the long range surface plasmon waveguide portion.

Preferably, an electrooptic dielectric material is employed for the aforementioned dielectric cover layer.

<Hybrid Coupling Structure of Short Range Surface Plasmon Polariton and Conventional Dielectric Waveguide>

The hybrid coupling structure of the short range surface plasmon polariton and the conventional dielectric waveguide provided by the present invention achieves high precision detection of the refractive index of a thin layer material, while the aforementioned structure is applied to a coupler, a polarizer and a refractive index detecting core chip, and solves such problems in a conventional detecting method that a volume is large, the number of required component devices is large, control is difficult, stability is inferior and detection sensitivity for an ultrathin layer material is low.

<Coupling Structure of Long Range Surface Plasmon Polariton and Dielectric Waveguide>

1. The coupling structure of the long range surface plasmon polariton and the dielectric waveguide provided by the present invention provides the base for attainment of high integration of a long range surface plasmon polariton-based device and a dielectric-based device as well as attainment of a refractive index-detectable and controllable photoelectric integrated device.

2. A refractive index sensor core chip to which the coupling structure of the long range surface plasmon polariton and the dielectric waveguide according to the present invention is applied has high sensitivity, and the aforementioned coupling structure is so applied that the aforementioned sensor has a small volume, requires a small number of component devices, is easy to control, and increased in stability.

3. The photoelectric intensity modulator to which the coupling structure of the long range surface plasmon polariton and the dielectric waveguide according to the present invention is applied has high sensitivity, is capable of implementing effective modulation on output power with a low driving voltage, and has low power consumption and high performance.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

<Hybrid Coupling Structure of Short Range Surface Plasmon Polariton and Conventional Dielectric Waveguide>

The present invention is now described with reference to Examples, which do not restrict the scope of the present invention.

A hybrid coupling structure of a short range surface plasmon polariton and a conventional dielectric waveguide is provided according to the present invention, and a dielectric substrate layer, a dielectric waveguide layer positioned on the dielectric substrate layer, a coupling matching layer positioned on the dielectric waveguide layer and a short range surface plasmon waveguide portion, formed on the coupling matching layer, for conducting the short range surface plasmon polariton are included in the aforementioned coupling structure.

The refractive index of the aforementioned dielectric waveguide layer is larger than the refractive index of the aforementioned dielectric substrate layer, and the refractive index of the aforementioned coupling matching layer is smaller than the refractive index of the aforementioned dielectric waveguide layer.

Further, selection of the refractive index of the aforementioned dielectric waveguide layer approximates or equalizes the equivalent refractive index of a base mode of a TM polarized state of the dielectric waveguide layer to or with the equivalent refractive index of the short range surface plasmon polariton.

Preferably, the refractive index of the aforementioned dielectric waveguide layer is 1.2 to 3.8, and the thickness of the aforementioned dielectric waveguide layer is 10 nm to 5000 nm.

The aforementioned short range surface plasmon waveguide portion includes a dielectric buffer layer, a metal layer and a dielectric cover layer successively formed from below.

The aforementioned metal layer is an alloy consisting of one type or a plurality of types among gold, silver, aluminum, copper, iron, chromium, nickel and titanium.

The thickness of the aforementioned metal layer is 10 nm to 100 nm, and the thickness of the aforementioned dielectric buffer layer is 10 nm to 5000 nm.

The refractive index of the aforementioned dielectric buffer layer is 1.2 to 3.8, and the refractive index of the aforementioned dielectric cover layer is 1.2 to 3.8.

The aforementioned coupling matching layer is a homogeneous dielectric material, and the total thickness of the aforementioned coupling matching layer and the aforementioned dielectric buffer layer is larger than a critical thickness stopping coupling development of the dielectric waveguide and the short range surface plasmon polariton.

Preferably, the thickness of the aforementioned coupling matching layer is 0.1 μm to 10 μm, and the refractive index of the aforementioned coupling matching layer is 1.2 to 3.8.

A coupling length at which the TM polarized state mode of the dielectric waveguide and the short range plasmon polariton develop coupling is 10 μm to 2000 μm.

Figure 1:
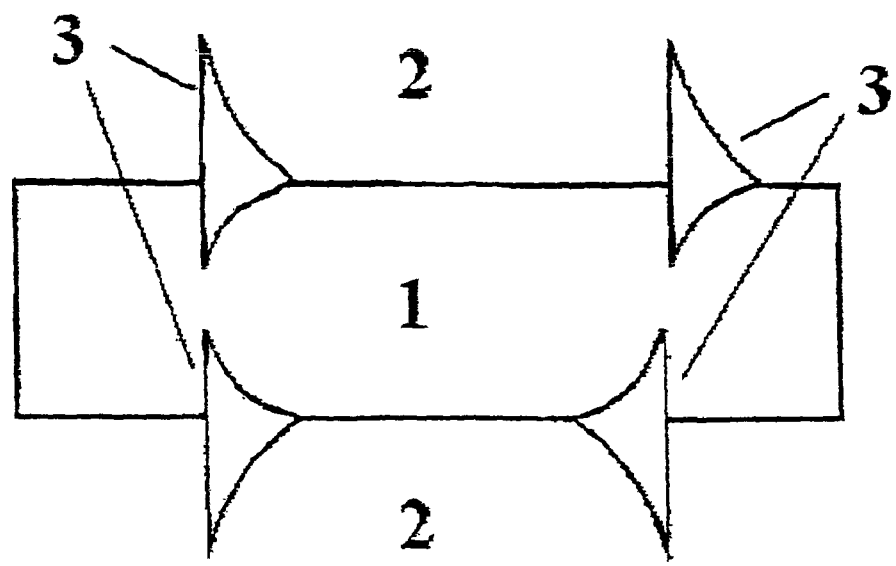
FIG. 1 is a conceptual diagram of surface plasmon polaritons.
Figure 2:
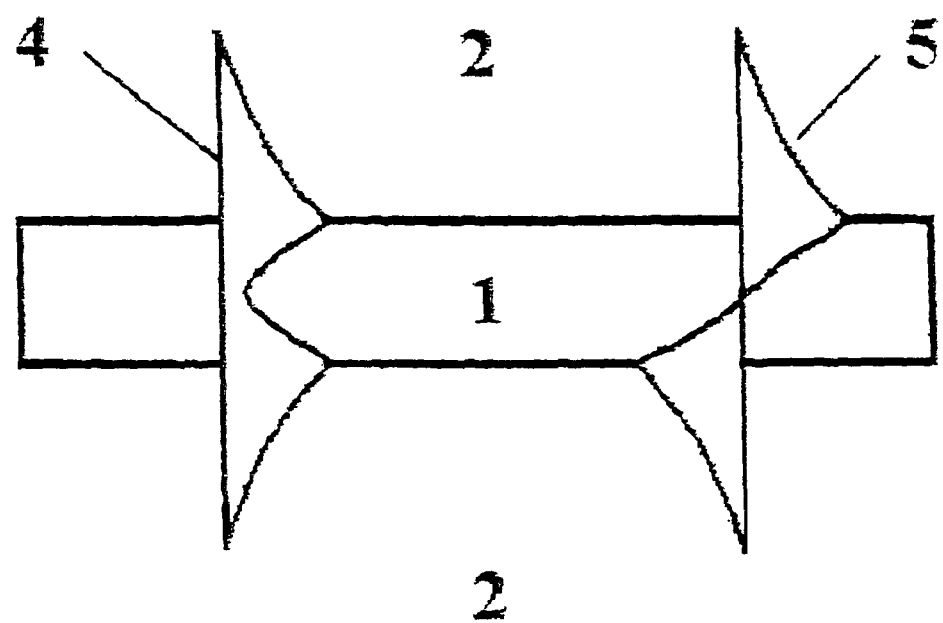
FIG. 2 is a conceptual diagram of the surface plasmon polaritons.
Figure 3:
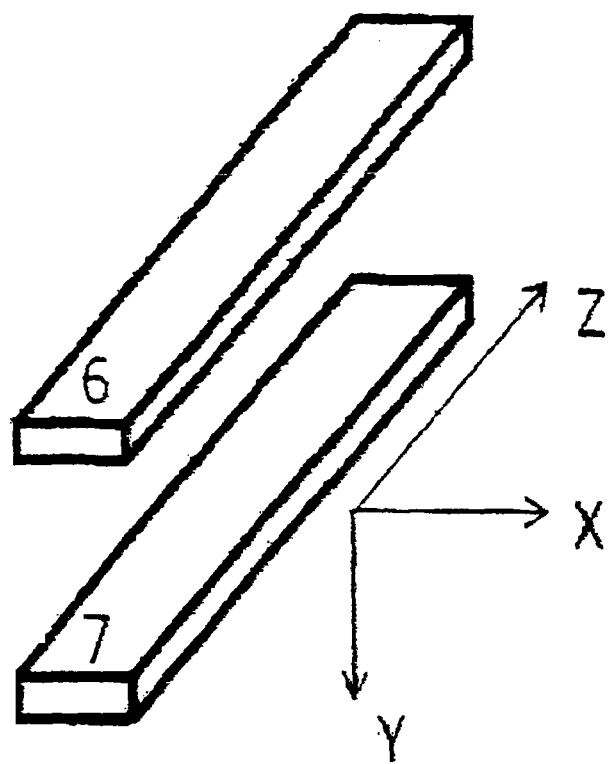
FIG. 3 is a diagram showing a core waveguide structure of a hybrid coupler of a short range surface plasmon polariton and a conventional dielectric waveguide.

Shown in FIG. 3 is a core waveguide structure of a coupler utilizing the aforementioned hybrid coupling structure. A metal waveguide (SRSPP) strip 6 and a dielectric strip 7 in the drawing are vertically arrayed, the propagation constants of modes conducted by a metal waveguide and a dielectric waveguide are basically equalized with each other when the widths and the thicknesses of metal waveguide strip 6 and dielectric strip 7 satisfy constant conditions, and the thicknesses of an intermediate coupling matching layer and a dielectric buffer layer are so controlled that coupling develops in the two modes and energy transfers between metal waveguide strip 6 and dielectric strip 7.

After passing through a plurality of coupling lengths, loss of the SRSPP mode relatively enlarges, and hence the energy of a TM wave rapidly attenuates. It is a TM polarization mode that the SRSPP waveguide of the metal strip conducts, and hence energy coupling of the dielectric waveguide mode and the SRSPP waveguide is limited to only TM polarization, while a TE polarized wave input from the dielectric strip does not couple to a metal arm but is merely transmitted along the dielectric strip, and finally output from the dielectric waveguide.

When utilizing different transmission characteristics with respect to two types of polarized states of the hybrid coupler, therefore, an advanced polarizer can be extremely easily implemented. One arm therein is the metal strip, and hence the same can also be regarded as an electric metal conductor in addition to the SRSPP waveguide. Thus, control with respect to an output of TM polarization can be implemented by applying a voltage to the metal conductor thereby altering the refractive index thereof through an electrooptic effect or a thermooptic effect of the dielectric around a metal film and controlling coupling between two arms of TM polarization.

When the refractive index of the dielectric above the metal film changes, on the other hand, optical power output from a dielectric arm changes and the mode field of the SRSPP highly approximates the metal film surface in addition thereto, whereby a change in the refractive index in a relatively thin range around the metal can be effectively detected, to provide a possibility for a high sensitivity ultrathin dielectric refractive index sensor. Besides, influences exerted on the mode field characteristics of the SRSPP by the refractive index difference between upper and lower dielectrics of the metal waveguide are relatively large, and hence the SRSPP mode is stopped if the refractive index difference between the upper and lower dielectrics of the metal film is relatively large. Therefore, the refractive index or the thickness of the dielectric buffer material layer under the metal film is so altered that an equivalent refractive index and a mode field distribution of SRSPP mode nonstop conditions can be altered while coupling efficiency for the dielectric waveguide mode and the SRSPP mode can also be altered, and the detection center and the dynamic range of the refractive index of the dielectric material above the metal of the sensor can be adjusted.

Figure 4:
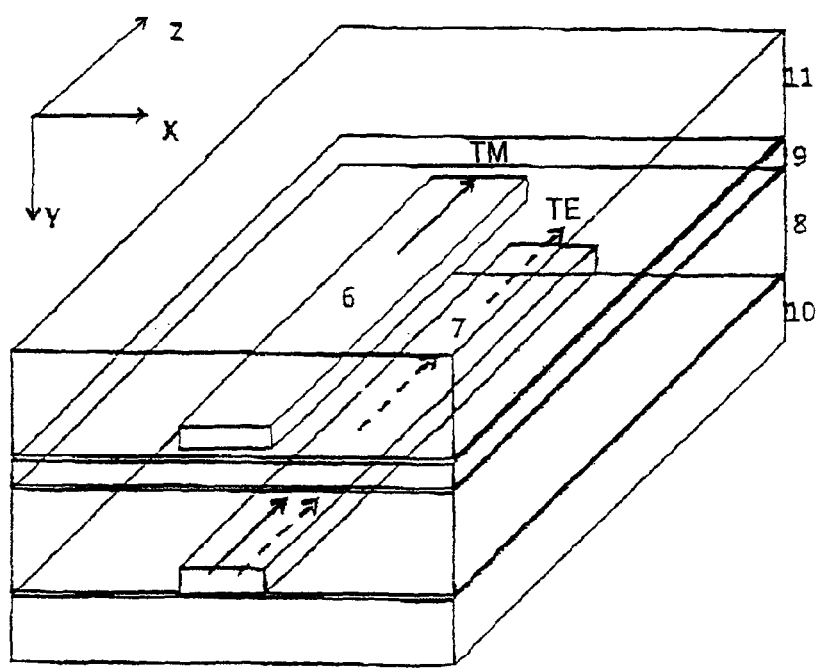
FIG. 4 is a stereoscopic structural sketch of one hybrid integrated coupler of a short range surface plasmon polariton and a conventional dielectric waveguide according to the present invention.
Figure 5:
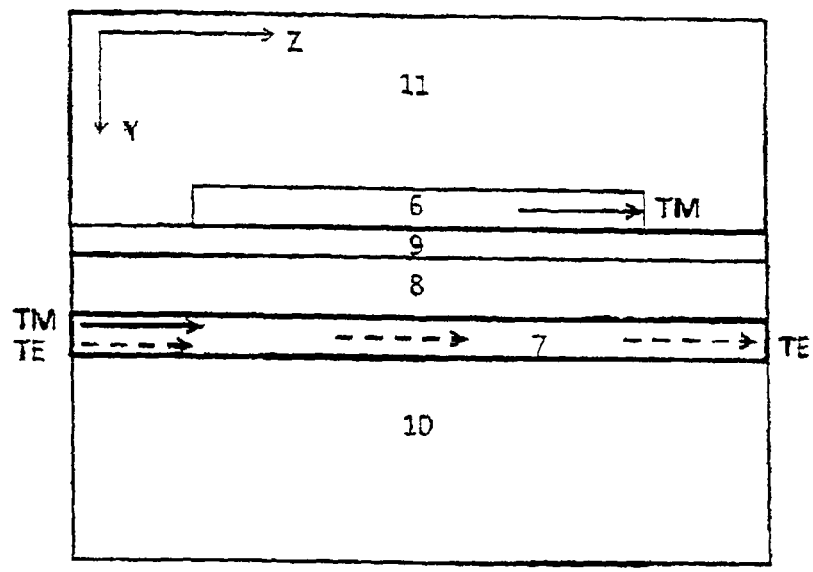
FIG. 5 is a side elevational view of FIG. 4.

Shown in FIG. 4 is a stereoscopic structural sketch of a hybrid coupler of a short range surface plasmon waveguide and a dielectric waveguide. A selected material for a dielectric substrate layer 10 and a dielectric cover layer 11 is $SiO_2$, and an $Si_3N_4$ strip 7 having a width of 1 μm and a thickness of 220 nm, a coupling matching layer 8 and a dielectric buffer layer 9 each made of $SiO_2$ with a thickness of 1.2 μm and an Au strip 6 having a width of 2 μm and a thickness of 15 nm are formed on a substrate by sputtering or vapor deposition and photoetching. The length of the coupler is 50 μm. When incident TM (solid line arrow) light and TE (broken line arrow) light are simultaneously input from dielectric strip 7 of the lower side, energy of a TM mode promptly couples into the metal waveguide of the upper side at a distance of 10-odd to several 10 μm. The TE light cannot develop coupling, but directly passes through the dielectric strip of the lower side. Therefore, the hybrid coupler can separate the TM light and the TE light from each other in an extremely short distance, as a highly integrable polarizer. Shown in FIG. 5 is a side elevational view of FIG. 4.

The Au strip in this Example can be replaced with any one of silver, aluminum, copper, titanium, nickel, chromium and iron or an alloy thereof, can also be provided as a metal ceramic strip, and is namely a mixture of the aforementioned metal or the alloy and a dielectric such as $SiO_2$, $MgF_2$, $Al_2O_3$, Si, GaAs or InP. While the dielectric material for the dielectric waveguide strip, the substrate, the cover layer and the dielectric buffer layer can be replaced with a resin material, $SiO_2$, $MgF_2$, $Al_2O_3$, Si, GaAs or InP, it is required that the refractive index of the dielectric waveguide strip is larger than the refractive indices of the peripheral dielectrics. When changing the material, constant adjustment must be performed on the geometric parameters of the metal (ceramic) strip and the dielectric strip.

Figure 6:
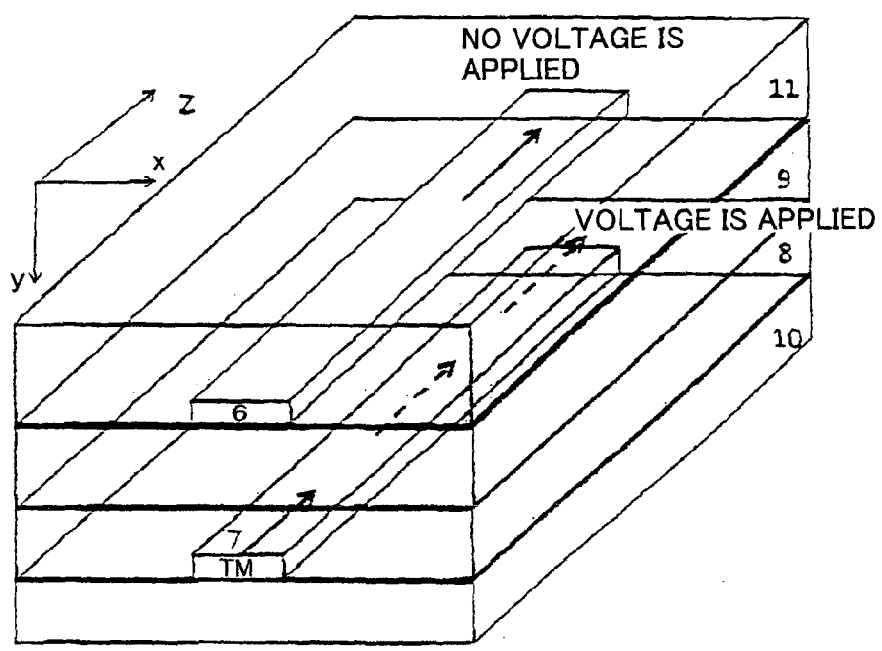
FIG. 6 is a stereoscopic structural sketch of another hybrid integrated coupler of a short range surface plasmon polariton and a conventional dielectric waveguide according to the present invention.
Figure 7:
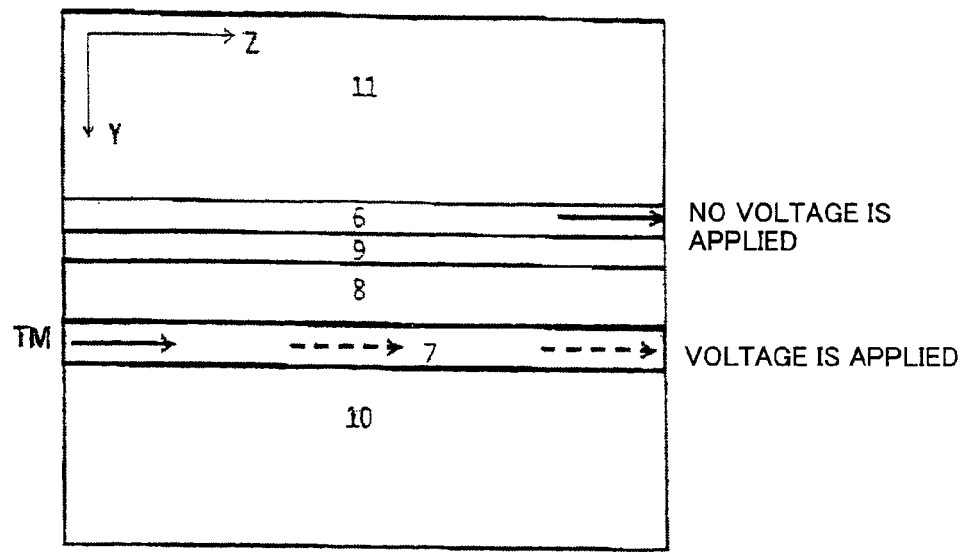
FIG. 7 is a side elevational view of FIG. 6.

Shown in FIG. 6 is a stereoscopic structural sketch of another hybrid coupler of a short range surface plasmon waveguide and a dielectric waveguide. A selected material for a dielectric substrate layer 10 and a dielectric cover layer 11 is BCB (benzocyclobutene), an $Si_3N_4$ strip 7 having a width of 1.5 μm and a thickness of 260 nm is formed thereon by sputtering or vapor deposition and photoetching, a coupling matching layer 8 and a dielectric buffer layer 9, in which the materials for single layers are identical to each other, having thicknesses of 1 μm are hardened, and an Au strip 6 having a width of 2 μm and a thickness of 15 nm is sputtered thereon. The length of the coupler is 20 μm. When no voltage is applied to metal waveguide strip 6, a TM mode of the dielectric waveguide of the lower side is converted to an SRSPP mode (as shown by solid arrow) of the upper surface metal strip. When a voltage is applied to the metal strip, the refractive index in the peripheral region of the metal strip of the resin material BCB in the periphery changes due to heat generation of a conductor, and hence a change is caused in the SRSPP mode characteristics. When the voltage is applied, incident light does no couple with the SRSPP waveguide again, but output along the dielectric waveguide of the lower side along arrow of a broken line. Therefore, the output of energy can be controlled by applying the voltage to the metal strip. At this time, the hybrid coupler can be used as a modulator, or a splitter or a polarizer. FIG. 7 is a side elevational view of FIG. 6.

Figure 8:
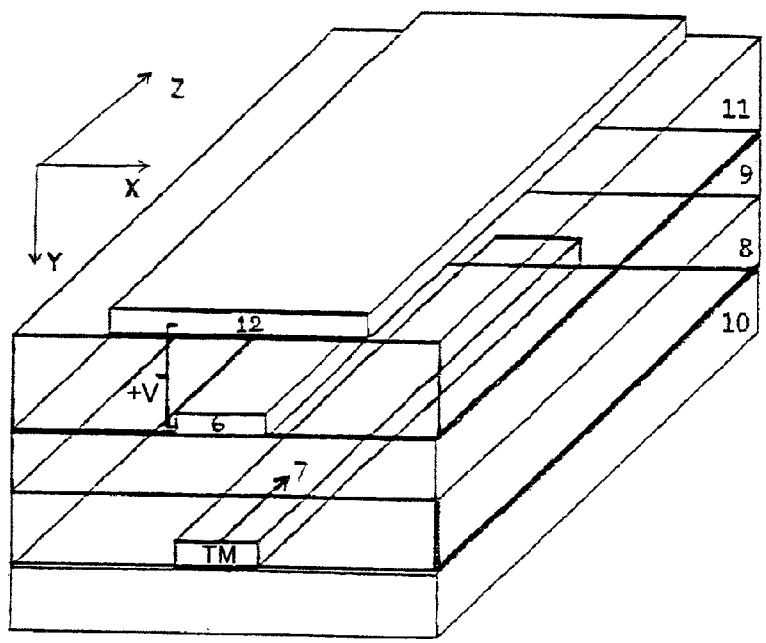
FIG. 8 is a stereoscopic structural sketch of still another controllable hybrid integrated coupler of a short range surface plasmon polariton and a conventional dielectric waveguide according to the present invention.
Figure 9:
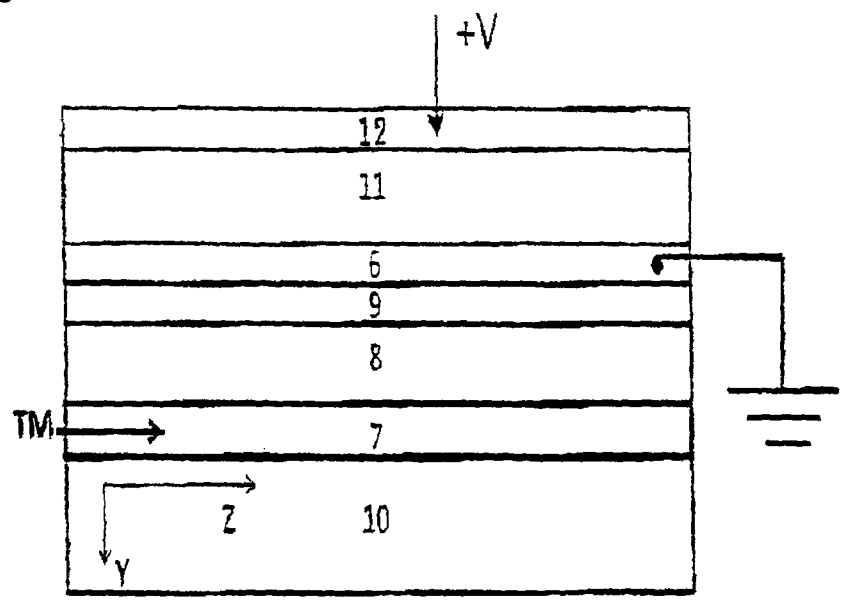
FIG. 9 is a side elevational view of FIG. 8.

Shown in FIG. 8 is a stereoscopic structural sketch of another hybrid coupler of a short range surface plasmon waveguide and a dielectric waveguide. A selected substrate dielectric material 10 is BCB, an $Si_3N_4$ strip 7 having a width of 1.5 μm and a thickness of 260 nm is formed thereon by sputtering or vapor deposition and photoetching, a coupling matching layer 8 and a dielectric buffer layer 9, in which the materials for single layers are identical to each other, having thicknesses of 1 μm are hardened, an Au strip 6 having a width of 2 μm and a thickness of 15 nm is sputtered thereon and grounded, a single-layer electrooptic polymer material is hardened above the Au strip as a dielectric cover layer 11, and a single-layer Au film 12 is finally vapor-deposited again as a positive electrode. The length of the coupler is 20 μm. When a voltage applied between metal waveguide strip 6 and metal film 12 changes, the refractive index of the material for dielectric cover layer 11 changes by an electrooptic effect following thereto, and conversion efficiency for a TM mode of the dielectric waveguide of the lower side and an SRSPP mode of metal waveguide strip 6 are altered, to alter a power output of the dielectric waveguide. Therefore, the output of power can be controlled by applying a voltage to the cover layer. At this time, the hybrid coupler can be used as a modulator, or a splitter or a polarizer. FIG. 9 is a side elevational view of FIG. 8.

Figure 10:
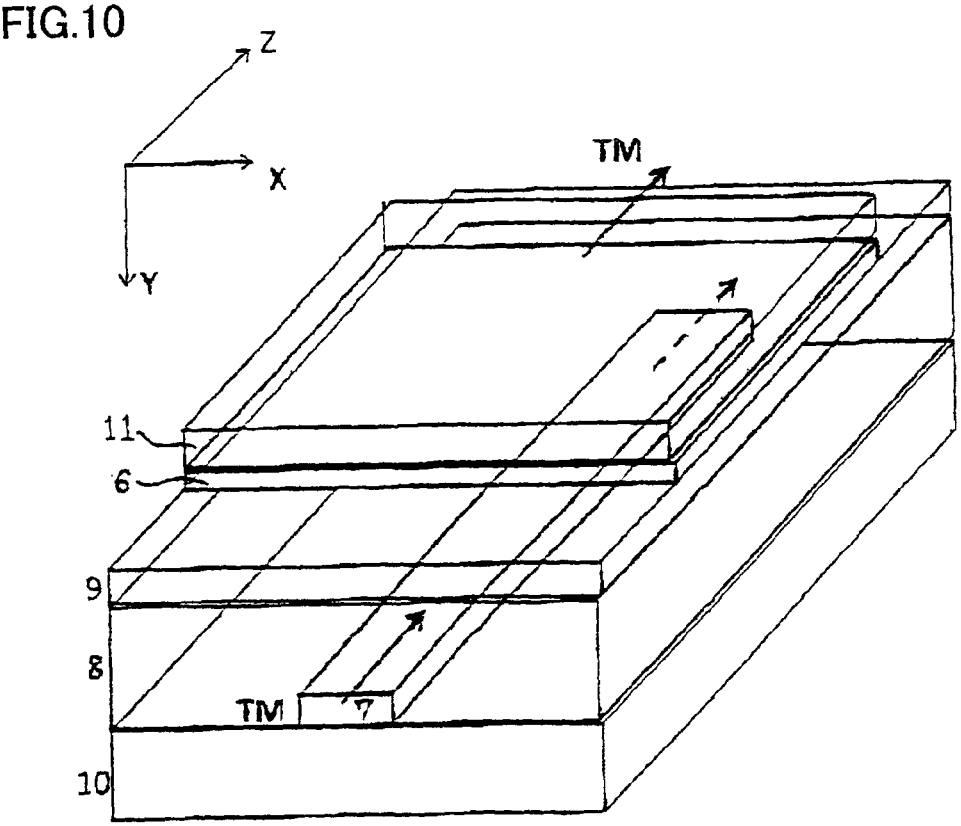
FIG. 10 is a stereoscopic structural sketch of one hybrid refractive index detecting core chip of a short range surface plasmon polariton and a conventional dielectric waveguide according to the present invention.
Figure 11:
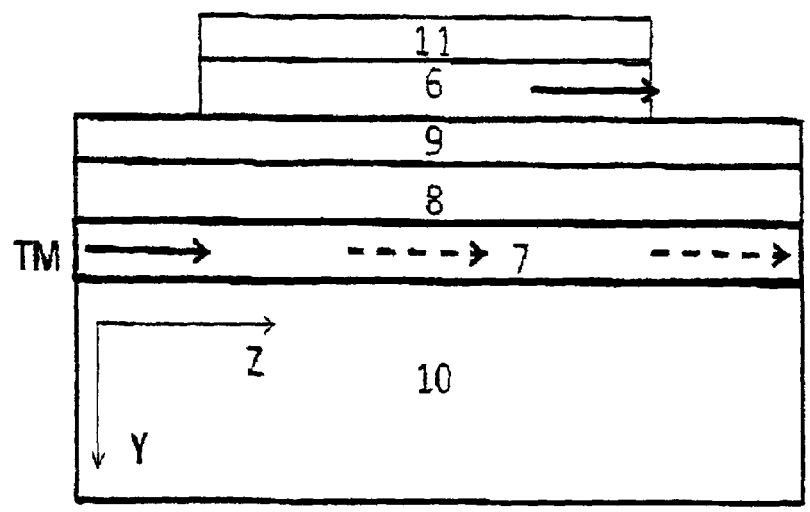
FIG. 11 is a side elevational view of FIG. 10.

Shown in FIG. 10 is a structural diagram of a hybrid coupling detecting core chip of a short range surface plasmon waveguide and a dielectric waveguide. A selected material for a dielectric substrate layer 10 is $SiO_2$, an $Si_3N_4$ strip 7 having a width of 8 μm and a thickness of 220 nm and a single-layer $SiO_2$ coupling matching layer 8 having a thickness of 1.5 μm are formed thereon by sputtering or vapor deposition and photoetching, thereafter a dielectric buffer layer 9 is formed by hardening a single-layer low refractive index resin material having a thickness of 500 nm, and a single-layer Au film 6 having a thickness of 30 nm is sputtered thereon. The propagation direction length of the core chip is 80 μm. Above metal film 6 is a detected substance in a water environment, and when the refractive index thereof changes following physical (temperature, humidity, pressure, electromagnetic field etc.) or biological/chemical factors (biochemical reaction), energy with which a dielectric arm of the lower side couples with the metal film of the upper side changes following the refractive index change in the detected substance above the metal film. The refractive index of a dielectric cover layer 11 exerts an influence on coupling between a TM mode of the dielectric and a short range surface plasmon polariton and further exerts an influence on the magnitude of TM output power of the dielectric waveguide, and hence a change in the refractive index of dielectric cover layer 11 above the metal surface can be detected by measuring a change in the output power of the dielectric waveguide. A small change in the refractive index of the aforementioned dielectric cover layer can be regarded as a small change in the refractive index of dielectric cover layer 11 caused by biological reactions of an antibody, antigen etc. having equivalent thicknesses or caused by physical or chemical action. A detectable refractive index range of the dielectric cover layer can be controlled by adjusting the refractive index and the thickness of the dielectric buffer layer. A wave mode field of the short range surface plasmon polariton highly approximates the metal film surface and a refractive index change in a relatively thin range around the metal can be effectively detected, and hence detection sensitivity is still extremely high if a detected dielectric is a thin-layer material, and the thickness of the measured dielectric can be reduced to not more than 100 nm.

Figure 12:
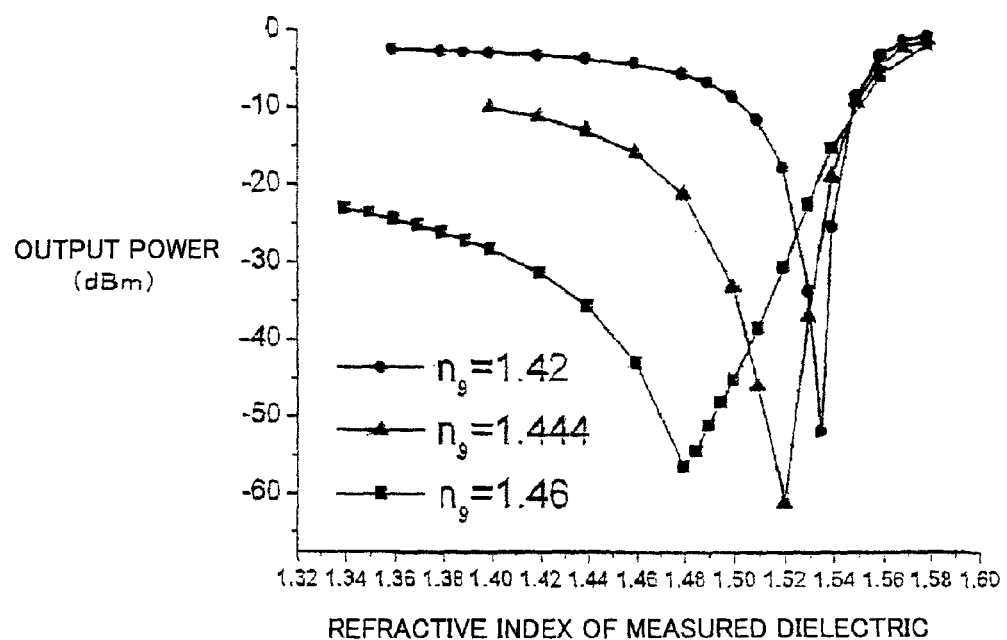
FIG. 12 is a change relation diagram of output power of one hybrid refractive index detecting core chip of a short range surface plasmon polariton and a conventional dielectric waveguide according to the present invention following the refractive index of a measured substance.

When the refractive index of a material CYTOP for the dielectric buffer layer is 1.42 and the thickness of dielectric cover layer 11 is 300 nm, for example, the relation of power output from the dielectric waveguide following the refractive index change in dielectric cover layer 11 is as shown by a circle point curve in FIG. 12 under a condition that the input in the dielectric waveguide is 0 dBm, information of the refractive index change in the detected dielectric can be obtained on the basis of a change in optical intensity output by a dielectric arm, the position of a detection center is 1.538 at this time, and assuming that the material for the buffer layer is identical to the substrate material and the coupling matching layer, i.e., 1.444, the detection center moves to 1.52 and a dynamic range of detection also increases at the same time, while sensitivity partially lowers as shown in a triangular curve in FIG. 12. When the refractive index of the dielectric buffer layer material is continuously increased up to 1.46, the detection center continuously moves to 1.48 toward a low refractive index direction as shown in a quadrangular curve in FIG. 12, while the dynamic range continuously increases, and the sensitivity further lowers.

An Au strip in this Example can be replaced with any one of silver, aluminum, copper, titanium, nickel, chromium and iron or an alloy thereof, can also be provided as a metal ceramic strip, and is namely a mixture of the aforementioned metal or the alloy and a dielectric such as $SiO_2$, $MgF_2$, $Al_2O_3$, Si, GaAs or InP. While the dielectric material for the dielectric waveguide strip, the substrate, the cover layer and the dielectric buffer layer can be replaced with a resin material, $SiO_2$, $MgF_2$, $Al_2O_3$, Si, GaAs or InP, it is required that the refractive index of the dielectric waveguide strip is larger than the refractive indices of the peripheral dielectrics. When changing the material, constant adjustment must be performed on the geometric parameters of the metal (ceramic) strip and the dielectric strip.

Figure 13:
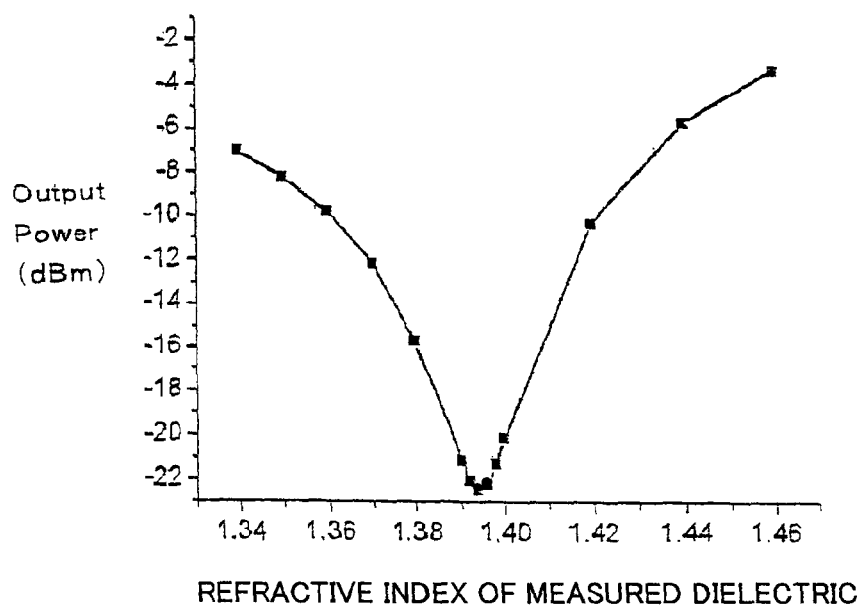
FIG. 13 is a change relation diagram of output power of another hybrid refractive index detecting core chip of a short range surface plasmon polariton and a conventional dielectric waveguide according to the present invention following the refractive index of a measured substance.

An example of hybrid coupling detection of the short range surface plasmon waveguide and the dielectric waveguide is as follows: Seventh, eighth and tenth layers are identical to FIG. 10. The thickness of a metal film of a sixth layer is 15 nm, and the refractive index of a coupling matching layer of a ninth layer is 1.38. The thickness of dielectric cover layer 11 is still 300 nm, and the propagation direction length is 70 μm. A change in output power following the refractive index of a detected substance is as shown in FIG. 13. At this time, the detection center lowers to around 1.38.

Figure 14:
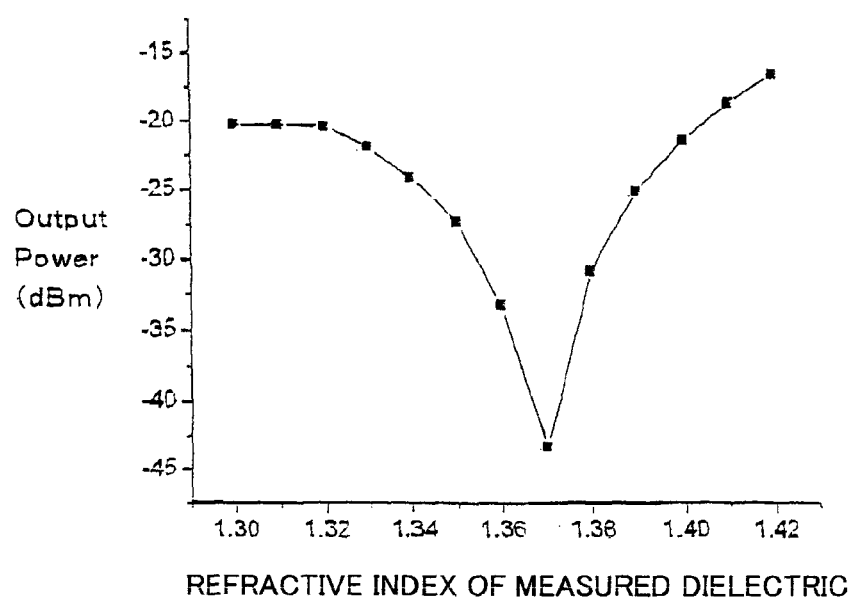
FIG. 14 is a change relation diagram of output power of still another hybrid refractive index detecting core chip of a short range surface plasmon polariton and a conventional dielectric waveguide according to the present invention following the refractive index of a measured substance.

An example of still another hybrid coupling detection of a short range surface plasmon waveguide and a dielectric waveguide is described as follows: The wavelength of incident light is 633 nm, selection of the material for a dielectric substrate layer 10 is a polymer material having a refractive index of 1.4, and an $Al_2O_3$ strip 7 having a width of 10 μm and a thickness of 150 nm is formed on a substrate by using photoetching and sputtering or deposition. A single polymer, having a thickness of 250 nm, of the same material as the tenth layer is hardened on the $Al_2O_3$ strip as a coupling matching layer, and a single-layer resin material (CYTOP) having a thickness of 50 nm and a refractive index of 1.36 is further hardened thereon as a buffer layer 9. Finally, an aluminum film having a thickness of 15 nm is sputtered on the ninth layer, above the aluminum film is a measured object having a thickness of 50 nm in a water environment, and the propagation direction length of a core chip is 50 μm. A change in output power following the refractive index of the detected object is as shown in FIG. 14. Also when the detection wavelength is shorter and the detected substance is thinner, high sensitivity can still be obtained, and an appropriate detection center is positioned around 1.37.

The aforementioned embodiments are merely for illustrating the present invention and do not restrict the present invention, and those skilled in the art can perform various types of changes without departing from the spirit and the scope of the present invention, and hence all equivalent technical ideas are regarded as belonging to the range of the present invention, and it is assumed that the patent protection range of the present invention is limited by the scope of claims for patent.

<Coupling Structure of Long Range Surface Plasmon Polariton and Dielectric Waveguide>

A coupling structure of a long range surface plasmon polariton and a dielectric waveguide and applications thereof provided by the present invention are described in detail with reference to the accompanying drawings and Examples as follows:

EXAMPLE 1

Figure 16:
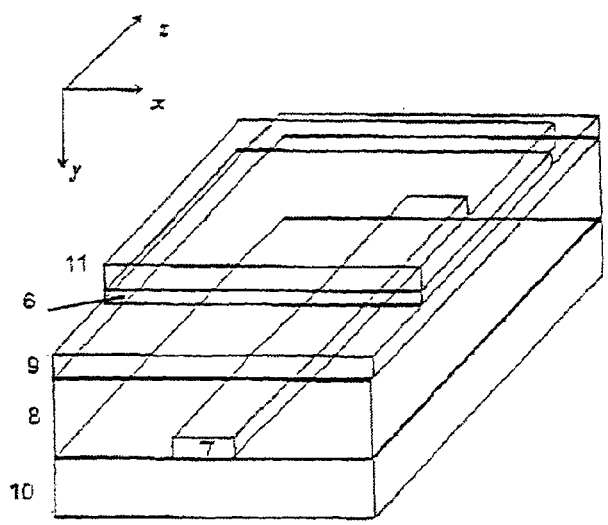
FIG. 16 is a structural sketch of a metal layer and a dielectric waveguide layer in the coupling structure of the long range surface plasmon polariton and the dielectric waveguide according to the present invention.
Figure 17:
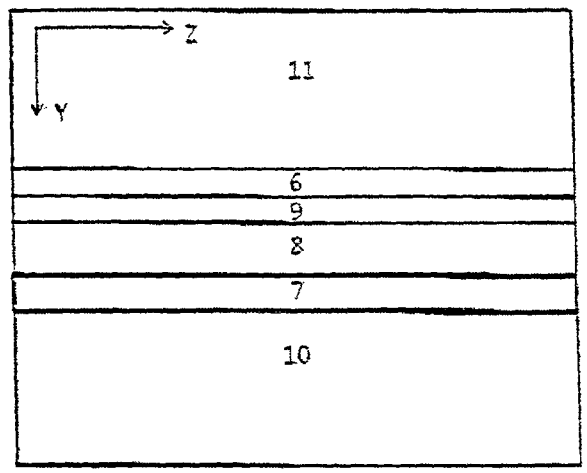
FIG. 17 is a structural sketch of the metal layer and the dielectric waveguide layer in the coupling structure of the long range surface plasmon polariton and the dielectric waveguide according to the present invention.

As to the coupling structure of the long range surface plasmon polariton and the dielectric waveguide provided by the present invention, this structure includes a dielectric substrate layer 10, a dielectric waveguide layer 7, a coupling matching layer 8, and a long range surface plasmon waveguide portion, formed on the coupling matching layer, for conducting the long range surface plasmon polariton, upward from below, as shown in FIGS. 16 and 17.

The refractive index of dielectric waveguide layer 7 is larger than the refractive index of dielectric substrate layer 10, and larger than the refractive index of coupling matching layer 8. Selection of the refractive index of dielectric waveguide layer 7 equalizes or relatively approximates the equivalent refractive index of a TM polarization base mode of the dielectric waveguide with or to the equivalent refractive index of the long range surface plasmon polariton. Preferably, the refractive index of dielectric waveguide layer 7 is 1.2 to 3.8 and the thickness thereof is 10 nm to 5000 nm, and the refractive index of coupling matching layer 8 is 1.2 to 3.8 and the thickness thereof is 0.01 μm to 10 μm.

The long range surface plasmon waveguide portion is divided into a dielectric buffer layer 9, a metal layer 6 and a dielectric cover layer 11 successively from below. Metal layer 6 is an alloy consisting of one type or a plurality of types among platinum, gold, silver, aluminum, copper, iron, chromium, nickel and titanium, or may be metal ceramic, and is namely a mixture of the aforementioned metal or the alloy and a dielectric such as $SiO_2$, $MgF_2$, $Al_2O_3$, Si, GaAs or InP, while the dielectric material for dielectric waveguide layer 7, dielectric substrate layer 10, dielectric cover layer 11 and dielectric buffer layer 9 can be prepared from a resin material, $SiO_2$, $MgF_2$, $Al_2O_3$, Si, GaAs or InP. The thickness of metal layer 6 is 5 nm to 100 nm, the thickness of dielectric buffer layer 9 is 10 nm to 20 μm, and the refractive indices of dielectric cover layer 11 and dielectric buffer layer 9 are 1.0 to 3.8. The total thickness of coupling matching layer 8 and dielectric buffer layer 9 is larger than a critical thickness stopping coupling development of a TM mode of the dielectric waveguide and a long range surface plasmon polariton mode.

Figure 15:
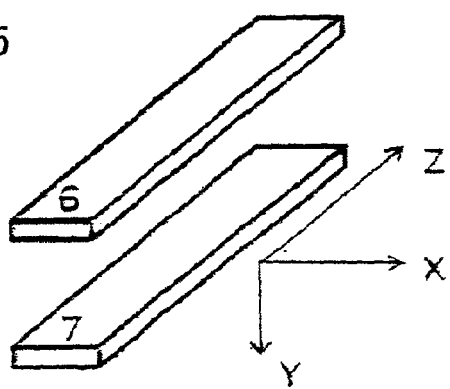
FIG. 15 is a structural sketch of a coupling structure of a long range surface plasmon polariton and a dielectric waveguide according to the present invention.

As shown in FIG. 15, two strips, i.e., a metal waveguide strip constituting metal layer (LRSPP waveguide) 6 and a dielectric strip constituting dielectric waveguide layer 7 are vertically arrayed. When the widths and the thicknesses of both layers are controlled to satisfy that the propagation constants of the LRSPP waveguide and a dielectric waveguide conduction mode are basically identical to each other, energy can be transferred between both layers by controlling the thicknesses of dielectric waveguide layer 7 and dielectric buffer layer 9 thereby developing coupling between an LRSPP mode and a TM mode of the dielectric waveguide.

When a change is caused in the refractive index of the dielectric above metal layer 6, loss of the LRSPP mode and mode field characteristics are influenced by that the refractive index of the dielectric under metal layer 6 is inferior, while the LRSPP mode is stopped if the difference between the refractive indices of upper and lower dielectrics of metal layer 6 is slightly large. The presence of the LRSPP and a change in the characteristics directly exert an influence on the coupling between the TM mode of the dielectric waveguide and the LRSPP mode, and further alters the magnitude of TM output power of the dielectric waveguide. Therefore, a change in the refractive index of dielectric cover layer 11 above metal layer 6 can be detected by measuring a change in the output power of the dielectric waveguide. Coupling efficiency between the modes is maximized if the refractive indices of the upper and lower dielectrics of metal layer 6 are extremely approximate to each other, and hence a detection center of the refractive index of the dielectric material above the metal layer of a refractive index sensor to which the coupling structure according to the present invention is applied can be adjusted by altering the refractive index of the material for dielectric buffer layer 9 under metal layer 6.

When actively altering the refractive index of the dielectric above the metal layer, the TM mode of the dielectric waveguide can also be controlled. Metal layer 6 can also be regarded as a metal conductor of electricity in addition to the LRSPP waveguide, and hence control with respect to an output of TM polarization can be implemented by applying a voltage to the metal conductor thereby altering the refractive index thereof through an electrooptic effect or a thermooptic effect of the dielectric around metal layer 6 and controlling coupling between the two layers of TM polarization.

EXAMPLE 2

Figure 18:
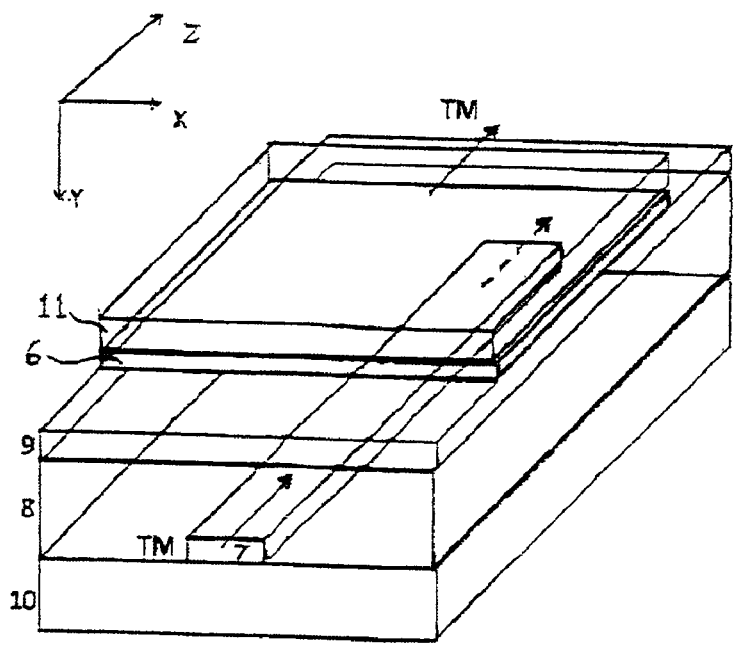
FIG. 18 is a structural sketch of a refractive index sensor of the coupling structure of the long range surface plasmon polariton and the dielectric waveguide according to the present invention.
Figure 19:
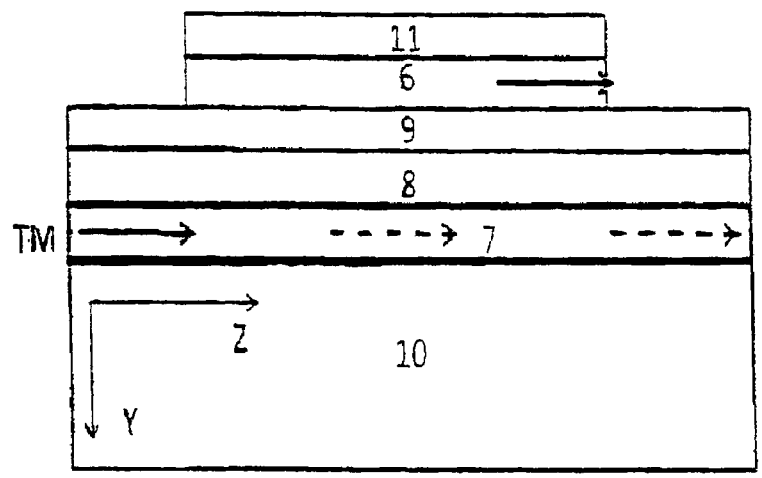
FIG. 19 is a structural sketch of the refractive index sensor of the coupling structure of the long range surface plasmon polariton and the dielectric waveguide according to the present invention.

Shown in FIGS. 18 and 19 are structural diagrams of a refractive index sensor to which the coupling structure of the long range surface plasmon polariton and the dielectric waveguide according to the present invention is applied, and the refractive index sensor is mainly constituted of the aforementioned coupling structure. The material for a dielectric substrate layer 10 is $SiO_2$, a dielectric waveguide layer 7 formed on dielectric substrate layer 10 by ultraviolet photoetching and chemical vapor deposition is an $Si_3N_4$ strip having a width of 2 μm and a thickness of 220 nm, both of a coupling matching layer 8 and a dielectric buffer layer 9 are made of $SiO_2$ having a refractive index of 1.45 with a total thickness of 6 μm, and a metal layer 6 prepared by ultraviolet photoetching and sputtering is an Al strip having a width of 5 μm, a length of 640 μm and a thickness of 25 nm.

Above metal layer 6 is a measured object, i.e., the dielectric cover layer, and when the refractive index thereof changes following physical (temperature, humidity, pressure, electromagnetic field etc.) or chemical (biochemical reaction) factors, energy with which dielectric waveguide layer 7 of the lower side couples with the Al strip of the upper side changes following the refractive index change in the detected substance above the Al strip.

Figure 20:
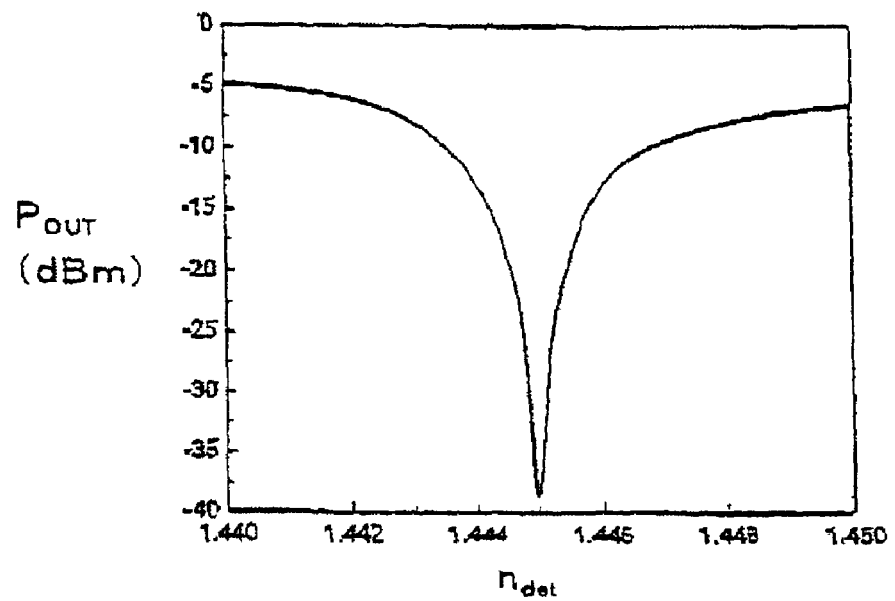
FIG. 20 is a change relation diagram of output power of the refractive index sensor to which the coupling structure of the long range surface plasmon polariton and the dielectric waveguide is applied following the refractive index of a measured substance.

A change $n_{det}$ in the refractive index of output power $P_{out}$ following dielectric cover layer 11 above metal layer 6 at a time when a TM wave having a wavelength of 1.55 μm and intensity of 0 dBm is input from dielectric waveguide layer 7 is as shown in FIG. 20. The detection center of the refractive index sensor, i.e., the lowest point in the curve is positioned around 1.45, i.e., positioned around the refractive index of dielectric buffer layer 9. A detection region is 1.444 to 1.446, and detection sensitivity can reach $5 \times 10^{-7}$.

The Al strip shown by metal layer 6 in this Example can be replaced with any one of gold, silver, copper, titanium, nickel, chromium and iron or an alloy thereof, and can also be provided as a metal ceramic strip, i.e., an alloy of the aforementioned metal or the alloy and a dielectric such as $SiO_2$, $MgF_2$, $Al_2O_3$, Si, GaAs or InP. While the dielectric material for dielectric waveguide layer 7, dielectric substrate layer 10, dielectric cover layer 11 and dielectric buffer layer 9 can be replaced with a resin material, $SiO_2$, $MgF_2$, $Al_2O_3$, Si, GaAs or InP, it is required that the refractive index of the material for dielectric waveguide layer 7 is larger than the refractive indices of the peripheral dielectrics. When changing the material, constant adjustment must be performed on the geometric parameters of the metal (ceramic) strip and a dielectric strip.

EXAMPLE 3

Shown in FIGS. 18 and 19 are structural diagrams of a refractive index sensor to which the coupling structure of the long range surface plasmon polariton and the dielectric waveguide according to the present invention is applied, and the refractive index sensor is mainly constituted of the aforementioned coupling structure. The material for a dielectric substrate layer 10 is $SiO_2$, a dielectric waveguide layer 7 formed on the substrate by ultraviolet photoetching and chemical vapor deposition is an $Si_3N_4$ strip having a width of 5 μm and a thickness of 120 nm, a coupling matching layer 8 is $SiO_2$ having a thickness of 3 μm, a dielectric buffer layer 9 is a CYTOP resin layer having a thickness of 4 μm and a refractive index of 1.38, and a metal layer 6 is an Au strip having a width of 20 μm, a length of 1050 μm and a thickness of 30 nm.

When the refractive index of a dielectric cover layer 11 above metal layer 6 changes following physical (temperature, humidity, pressure, electromagnetic field etc.) or chemical (biochemical reaction) factors, energy with which dielectric waveguide layer 7 of the lower side couples with metal layer 6 of the upper side changes following the refractive index change in dielectric cover layer 11 above metal layer 6.

Figure 21:
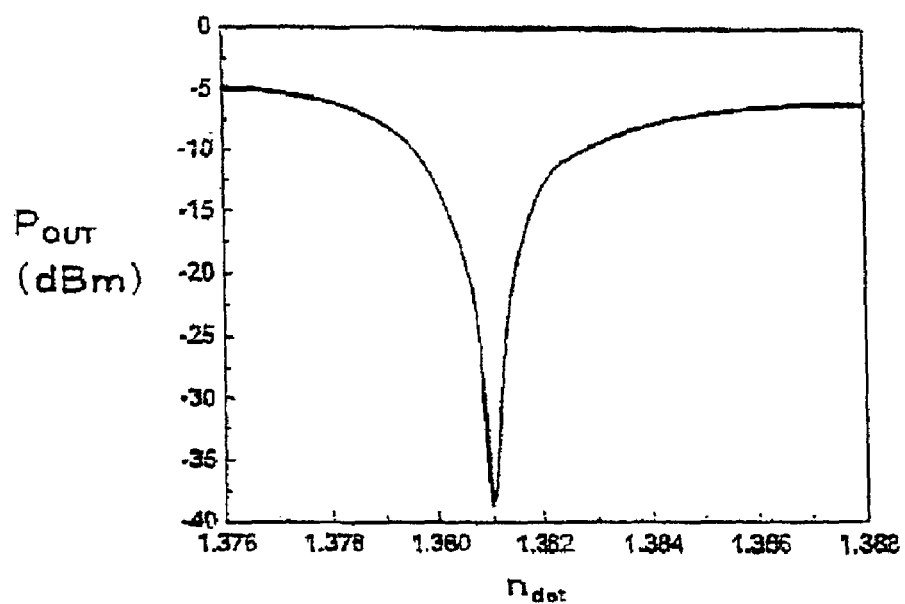
FIG. 21 is a change relation diagram of output power of a refractive index sensor to which another coupling structure of a long range surface plasmon polariton and a dielectric waveguide is applied following the refractive index of a measured substance.

A change $n_{det}$ in the refractive index of output power $P_{out}$ following dielectric cover layer 11 above the metal at a time when a TM wave having a wavelength of 1.55 μm and intensity of 0 dBm is input from the dielectric waveguide layer is as shown in FIG. 21. The detection center thereof i.e., the lowest point in the curve is positioned around 1.38, i.e., positioned around the refractive index of dielectric buffer layer 9.

A detection region is 1.380 to 1.382, and detection sensitivity can reach $6 \times 10^{-7}$.

Other selection of materials is identical to Example 2.

EXAMPLE 4

Shown in FIGS. 18 and 19 are structural diagrams of a refractive index sensor to which the coupling structure of the long range surface plasmon polariton and the dielectric waveguide according to the present invention is applied. A glass material having a refractive index of 1.45 is selected as the material for a dielectric substrate layer 10, and a dielectric waveguide layer 7 having a width of 2 μm and a refractive index of 1.46 is formed on the substrate by using photoetching and an ion exchange method. A coupling matching layer 8 is $SiO_2$ having a thickness of 1 μm, a resin material having a thickness of 1 μm and a refractive index of 1.36 is deposited thereon as a dielectric buffer layer 9, and a metal layer 6 is an Al film having a length of 640 μm and a thickness of 30 nm.

Above the Al film is a dielectric cover layer 11 having a thickness of 0.5 μm, and when the refractive index thereof changes following physical (temperature, humidity, pressure, electromagnetic field etc.) or chemical (biochemical reaction) factors, energy with which dielectric waveguide layer 7 of the lower side couples with the Al film of the upper side changes following a refractive index change in a detected substance above the metal film.

A change in the refractive index of output power following a dielectric detection layer above the metal at a time when a TM wave having a wavelength of 0.633 μm and intensity of 0 dBm is input from the dielectric waveguide layer is similar to FIGS. 20 and 21. A different point is such a point that the detection center thereof, i.e., the lowest point in the curve is positioned around 1.36, i.e., positioned around the refractive index of the dielectric buffer layer. A detection region is 1.359 to 1.361, and detection sensitivity can reach $5 \times 10^{-7}$.

Other selection of materials is identical to Example 2.

EXAMPLE 5

Figure 22:
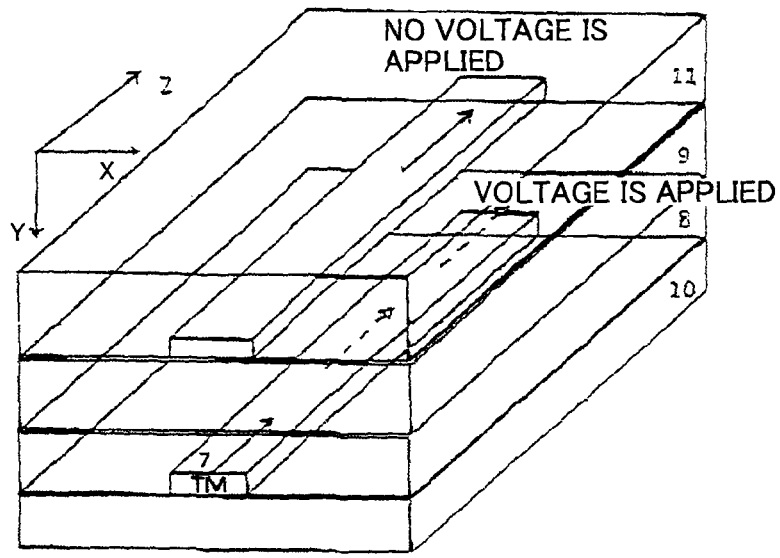
FIG. 22 is a structural sketch of a photoelectric variable attenuator to which the coupling structure of the long range surface plasmon polariton and the dielectric waveguide is applied.
Figure 23:
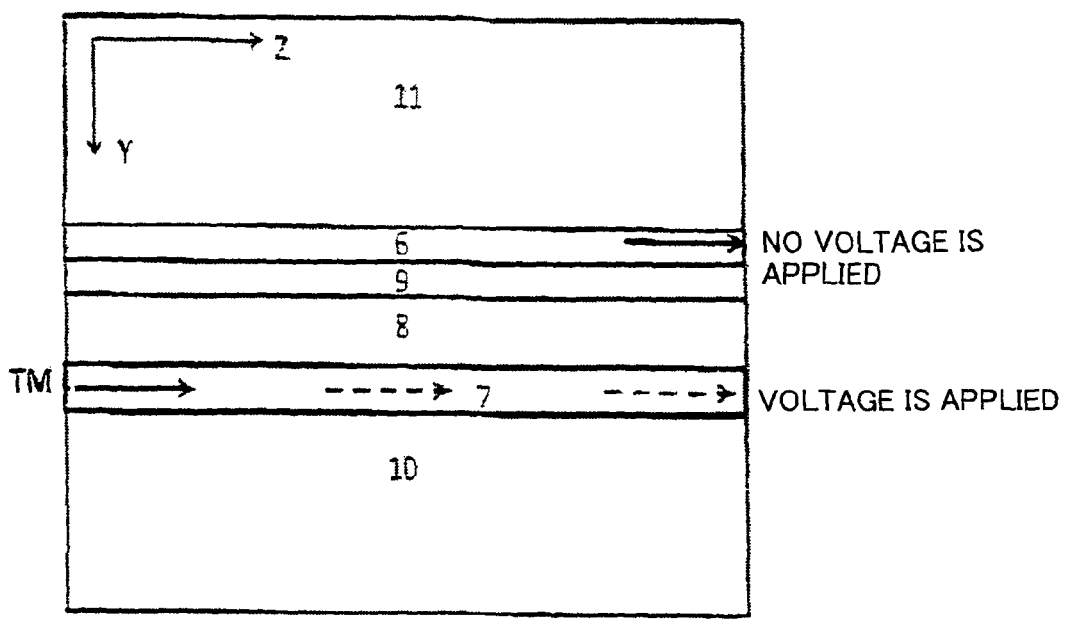
FIG. 23 is a structural sketch of the photoelectric variable attenuator to which the coupling structure of the long range surface plasmon polariton and the dielectric waveguide is applied.

Shown in FIGS. 22 and 23 is a basic structure of a thermooptic variable attenuator to which the coupling structure of the long range surface plasmon polariton and the dielectric waveguide according to the present invention is applied. The thermooptic attenuator is mainly constituted of the aforementioned coupling structure, the material for a dielectric substrate layer 10 is $SiO_2$, an $Si_3N_4$ strip having a width of 2 μm and a thickness of 220 nm is formed thereon by sputtering or vapor deposition and photoetching as a dielectric waveguide layer 7, single-layer $SiO_2$ having a thickness of 6 μm is continuously deposited as a coupling matching layer 8 and a dielectric buffer layer 9, a metal layer 6 sputtered thereon is an Al strip having a width of 5 μm and a thickness of 25 nm while the length thereof is 1140 μm, and finally a resin material having a thickness of 10 μm whose refractive index is extremely close to $SiO_2$ and changes following a temperature is applied as a dielectric cover layer 11.

When a TM wave having a wavelength of 1.55 μm and intensity of 0 dBm is input from dielectric waveguide layer 7 and no voltage is applied to metal layer 6, a TM mode of the dielectric waveguide of the lower side is converted to an LRSPP mode (shown by solid arrow) of the Al strip of the upper surface. When a voltage is applied to the Al strip, the refractive index of peripheral dielectric cover layer 11 in a peripheral region of the Al strip changes due to heat generation of a conductor, and hence a change is caused in LRSPP mode characteristics. When the voltage is applied, incident light does not couple the LRSPP waveguide again, but is output along the dielectric waveguide of the lower side along arrow of a broken line. Therefore, the magnitude of output power $P_{out}$ of dielectric waveguide layer 7 can be controlled by applying the voltage to the Al strip.

Other selection of materials is identical to Example 2.

EXAMPLE 6

Figure 24:
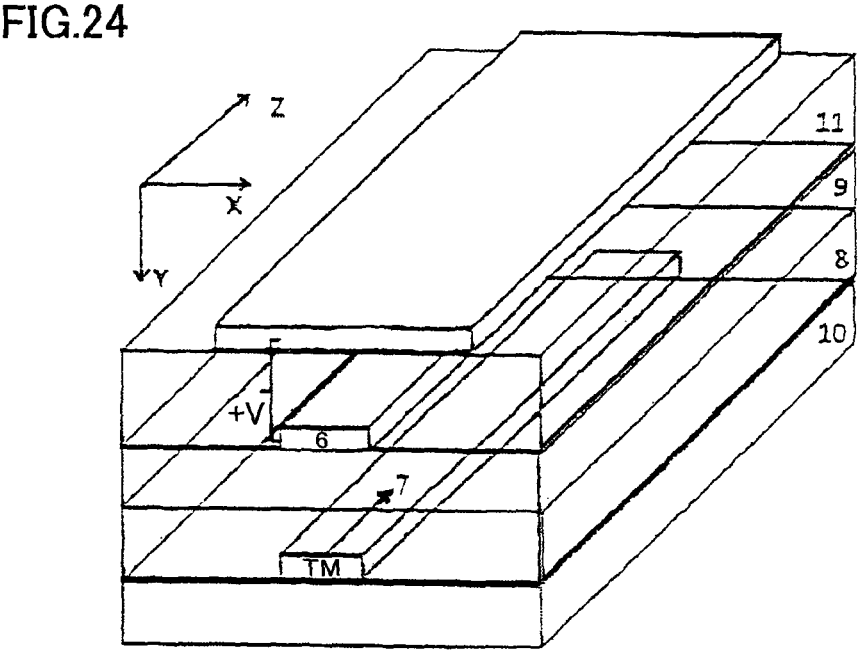
FIG. 24 is a structural sketch of a photoelectric intensity modulator to which the coupling structure of the long range surface plasmon polariton and the dielectric waveguide according to the present invention is applied.
Figure 25:
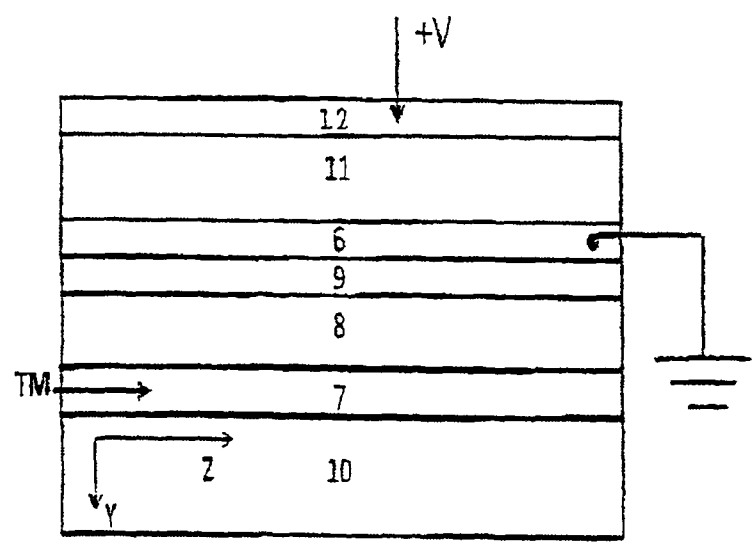
FIG. 25 is a structural sketch of the photoelectric intensity modulator to which the coupling structure of the long range surface plasmon polariton and the dielectric waveguide according to the present invention is applied.

Shown in FIGS. 24 and 25 is a basic structure of a photoelectric intensity modulator to which the coupling structure of the long range surface plasmon polariton and the dielectric waveguide according to the present invention is applied. The modulator is mainly constituted of the aforementioned coupling structure. The material for a dielectric substrate layer 10 is $SiO_2$, an $Si_3N_4$ strip having a width of 2 μm and a thickness of 220 nm is formed thereon by sputtering or vapor deposition and photoetching as a dielectric waveguide layer 7, single-layer $SiO_2$ having a thickness of 6 μm is continuously deposited as a coupling matching layer 8 and a dielectric buffer layer 9, a metal layer 6 prepared by sputtering Al thereon has a width of 5 μm, a thickness of 25 nm and a length of 1140 μm, and thereafter a dielectric cover layer 11 is prepared from an electrooptic material 11 having a thickness of 4 μm whose refractive index is extremely close to $SiO_2$, while a metal electrode 12 is prepared from an Au film.

A TM wave having a wavelength of 1.55 μm and intensity of 0 dBm is input from dielectric waveguide layer 7. When power applied between metal layer 6 and Au film metal electrode 12 changes, the refractive index of the material for dielectric cover layer 11 changes following thereto due to an electrooptic effect, whereby a TM mode of the dielectric waveguide of the lower side couples with an LRSPP mode of metal layer 6, and further alters a power output of the dielectric waveguide. Therefore, intensity modulation can be executed on output power of the dielectric waveguide by applying a modulation voltage to dielectric cover layer 11.

The coupling structure of the long range surface plasmon polariton and the dielectric waveguide in this Example can also be used as a modulator, or a splitter or a polarizer.

Other selection of materials is identical to Example 2.

DESCRIPTION OF THE REFERENCE CHARACTERS 1 metal (or mixture of metal and dielectric), 2 dielectric around metal, 3 surface plasmon polariton (on interfacial position), 4 long range surface plasmon polariton, 5 short range surface plasmon polariton, 6 metal waveguide strip (metal layer), 7 dielectric strip (dielectric waveguide layer), 8 coupling matching layer, 9 dielectric buffer layer, 10 dielectric substrate layer, 11 dielectric cover layer, 12 metal film (metal electrode).

Although the present invention has been described and illustrated in detail, it is clearly understood that the same is by way of illustration and example only and is not to be taken by way of limitation, the scope of the present invention being interpreted by the terms of the appended claims.

What is claimed is:
1. A TM polarization modulator to which a hybrid coupling structure of a short range surface plasmon polariton and a conventional dielectric waveguide is applied,
   wherein the hybrid coupling structure comprises:
      a dielectric substrate layer;
      a dielectric waveguide layer positioned on said dielectric substrate layer;

a coupling matching layer on said dielectric waveguide layer; and a short range surface plasmon waveguide portion, on said coupling matching layer, for conducting the short. range surface plasmon polariton, the short range surface plasmon waveguide portion including a dielectric cover layer, wherein an upper portion of said dielectric cover layer is covered with an electrode consisting of gold and chromium, and modulation of TM polarization is implemented by applying a modulation voltage between the electrode and the metal layer in the short range surface plasmon polariton waveguide portion and further executing modulation on a power output of the dielectric waveguide.

2. The TM polarization modulator according to claim 1, wherein an electrooptic dielectric material is employed for said dielectric cover layer.

* * * * *